United States Patent [19]
Wu et al.

[11] Patent Number: 4,704,278
[45] Date of Patent: * Nov. 3, 1987

[54] FLUIDIZED MAGALDRATE SUSPENSION

[75] Inventors: Chien-Chin Wu, Wilmington, Del.; Gerald L. Reuter, Plattsburgh, N.Y.

[73] Assignee: American Home Products Corp (Del), New York, N.Y.

[ * ] Notice: The portion of the term of this patent subsequent to Jun. 30, 2004 has been disclaimed.

[21] Appl. No.: 895,012

[22] Filed: Aug. 8, 1986

Related U.S. Application Data

[63] Continuation of Ser. No. 661,648, Oct. 17, 1984, abandoned.

[51] Int. Cl.$^4$ ............................................. A61K 33/08
[52] U.S. Cl. ..................................... 424/157; 424/158
[58] Field of Search ................................ 424/157, 158

[56] References Cited

U.S. PATENT DOCUMENTS

| | | | |
|---|---|---|---|
| 4,112,072 | 9/1978 | Rubino et al. | 424/158 |
| 4,115,553 | 9/1978 | Rubino et al. | 424/158 |
| 4,117,116 | 9/1978 | Buehler et al. | 424/158 |

OTHER PUBLICATIONS

*Handbook on Nonprescription Drugs*, Fifth Edition (1977), p. 16, American Pharmaceutical Assoc., Wash. D.C.

Primary Examiner—Frederick E. Waddell

[57] ABSTRACT

An aqueous antacid composition of magaldrate gel and a process for preparing same are described by the invention. The composition is prepared from and contains precipitated and undried magaldrate gel and a fluidizing of a first and second fluidizer. On fluidizer is provided by an aluminum hydroxide gel having colloidal properties and the second by a pharmaceutically acceptable citrate ion source including citric acid. The process and composition are characterized in providing a fluid, resuspendible, pharmaceutically elegant suspension possessing high antacid capacity and stability at even elevated magaldrate concentrations in addition to the ability to fluidize stiff, paste-like magaldrate gel cakes.

3 Claims, No Drawings

FLUIDIZED MAGALDRATE SUSPENSION

This is a continuation of application Ser. No. 661,648, filed Oct. 17, 1984, now abondoned.

BACKGROUND OF THE INVENTION

1. Field of the Invention

This invention relates to resuspendible, pharmaceutically elegant high concentration, low viscosity, aqueous antacid suspension dosage forms for oral administration and to methods for their preparation and use.

2. Decription of the Antacid Art

Antacids are widely used in the treatment of gastrointestinal disorders. Their effectiveness in promoting the healing of gastric and duodenal ulcers has been well documented. Essentially, antacids exert their positive effects by neutralizing the gastric acid secreted in the stomach. When the pH of stomach contents is raised above 3, most gastric acid is neutralized and the proteolytic activity of pepsin is inhibited. The recent elevation of antacids to a major therapeutic role, particularly in ulcer therapy, rather than a merely pallative role, has emphasized the importance of providing antacid products featuring a high neutralization (and buffer) capacity as well as a rapid rate of gastric acid neutralization. These features particularly that of rapid rate of neutralization to the neutralization capacity of the antacid define the more effective antacid in vivo since it is less likely that unconsumed antacids will be removed by normal gastric emptying.

Most antacids are available in both liquid and solid dosage forms. The liquid antacids, as aqueous suspensions, are, generally, more effective than the same antacids in solid dosage forms and are more commonly prescribed in the hospital. The greater effectiveness of liquid antacids is partially due to the large surface area available in liquid suspensions to react with gastric acid and partially due to the great amount of colloidal particles in aqueous suspension which can more easily reach the affected area where treatment is needed. Moreover, aqueous suspensions of undehydrated antacids are more reactive than dry or solid antacids.

While liquid antacids possess these advantages, the same require administration of relatively large volumes of liquid suspension. The ingestion of such large volumes is inconvenient, however, making the normal problem of assuring patient compliance outside the hospital environment even more difficult. Since high dose regimes of liquid antacid have recently been shown to be effective both in promoting the healing of duodenal ulcers and in preventing the acute upper gastrointestinal bleeding in critically ill patients, the use of regular liquid antacid suspensions with the usual solid antacid content in the 6-12 percent range has become even more impractical for such therapeutic indications.

The most widely used antacids can be described as mineral type, insoluble inorganic salts that are hydrated, possess colloidal properties, and contain, for example, aluminum, magnesium, bismouth and the like. Compounds of the described mineral variety in their freshly prepared, hydrated form and in suspensions therefrom provide some of the characteristics desired in an antacid. To provide liquid antacids with a high neutralization capacity it is necessary to increase the solids concentration of the antacid components. Such increases in concentration, however, are accompanied at higher levels with exponential increases in viscosity, a loss in colloidal properties and a loss of fluidity or mobility. Even where fluidity is initially maintained or achieved, further requirements of pharmaceutically acceptable aqueous antacid suspensions call for a smooth (non-gritty) mouth feel and maintenance of a gel structure for both suspendibility and resuspendibility. In general, resuspendible, aqueous antacid suspensions are typically de-flocculated products which contain a deflocculant or suspending agent to arrest or control further agglomeration or flocculation and settling. In the absence of a deflocculant or suspending agent type additive, the antacid in a suspension forms a hard cake or a gel structure which can no longer be resuspended with its original desirable characteristics. The formation of such a cake or gel structure is independent of antacid concentration except for low antacid concentration.

The deflocculants and suspending agents have been frequently included in the formulation of aqueous antacid suspensions containing solid antacid concentrations in the range of about 6 to 12 percent to prevent caking. With the growing interest in providing antacid suspension dosage forms with a greater acid neutralizing capacity, means were sought to provide highly concentrated but fluid systems.

U.S. Pat. No. 3,579,634 describes an antacid composition containing as the essential ingredients an antacid and a water dispersible, colloidal anionic ether or ester derivative of a low polymer of a monosaccharide as a gelation agent, the gelation agent being such that a thickened gel-like consistency occurs upon interaction of the composition with gastro-intestinal mucous so as to adhere thereto. The gelation agent in vitro is described as providing fluidity to concentrated suspensions, and the starting actacid may be selected from powder, granule or paste forms of certain calcium, aluminum, magnesium, sodium and bismouth antacids. The antacid suspension compositions disclosed therein appear to initially require milling, high energy agitation or homogenization to eliminate the grittiness of the antacid ingredient.

In U.S. Pat. No. 3,591,680, high concentration antacid suspensions are disclosed containing about 25 to 50 percent weight/volume of certain selected solid antacid materials suspended in an aqueous vehicle containing certain specified suspending agents of which a defind hydroxypropyl cellulose is preferred. While these suspension are said to provide stable and palatable, high concentration suspensions, the preferred composition is stated to provide only a minimum of 2 months of continued fluidity and pourability. Such standards are not acceptable for a commercial product in which shelf life stability should extend for at least 1-2 years.

U.S. Pat. No. 3,347,744 discloses a high concentration magnesium hydroxide suspension containing up to 30% of that antacid with a cellulosic suspending agent and submicroscopic silica. The suspension is said to avoid the clumping and caking common among even lower concentration magnesium hydroxide suspensions, although there is no disclosure that the suspension is thereby rendered more fluid.

More recently, in U.S. Pat. No. 4,117,116, there is disclosed a method for lowering the viscosity of a commercially available aqueous antacid gel cake to render the same pumpable in the production environment. The gel cake represents a magnesium hydroxide antacid, an aluminum hydroxide antacid or a mixture thereof and the antacid is 25-35% weight by weight of the gel cake before processing. The method comprises mixing into the gel cake a fluidizing agent selected from acacia, citric acid, sodium citrate, sodium lauryl sulfate or dioctyl sodium sulfosuccinate and the fluidizing agent amounts to 0.1-4% of the final total mixture.

It is an object of this invention to provide magaldrate, aqueous antacid suspensions with high antacid capacity and good mouth feel characteristics.

Another object of this invention is to provide magaldrate, aqueous antacid suspensions with high antacid capacity and which retain, at high concentrations, the desirable qualities of rapid acid neutralization and reliably uniform reaction in acidic solutions.

A further object of the invention is to provide high antacid capacity, aqueous magaldrate suspensions with good fluidity, pourability and suspension characteristics and which further provides full resuspendibility under the typical shelf life conditions for a commercial aqueous antacid suspension.

SUMMARY OF THE INVENTION

In accordance with this invention there is provided aqueous antacid compositions characterized in providing a fluid, resuspendible, pharmaceutically elegant antacid suspension with high antacid capacity. The composition comprises precipitated and undried magaldrate gel and a fluidizing amount of a combination of an aluminum hydroxide gel having colloidal properties as a first fluidizer and a second fluidizer selected from at least one from the group consisting of citric acid and a pharmaceutically acceptable citrate ion source.

In another embodiment, the invention includes a method for producing aqueous antacid composition of high antacid capacity and which are characterized in providing fluid, resuspendible pharmaceutically elegant antacid suspensions of magaldrate. The method comprises mixing a precipitated and undried magaldrate gel with a fluidizing combination of a first and second fluidizer. The first fluidizer is selected from an aluminum hydroxide gel having colloidal properties and the second fluidizer is selected from at least one from the group consisting of citric acid and a pharmaceutically acceptable citrate ion source. The method for producing the high antacid capacity, aqueous antacid compositions of the invention may be broadly approached and achieved, for example, either by prior concentration of the magaldrate gel cake into a high concentration paste followed by its fluidization with a fluidizing amount of the combination of the first and second fluidizer, or, by concentration of a fluid and relatively low concentration magaldrate gel cake previous mixed with a fluidizing amount of the combination of the first and second fluidizer.

The magaldrate of the invention is the precipitated, undried form of the antacid. This description refers to magaldrate gel which has not been previously dried to its hydrated, anhydrous form.

DETAILED DESCRIPTION OF THE INVENTION

Magaldrate is a chemical combination of aluminum and magnesium hydroxide, corresponding approximately to the formula $Al_5Mg_{10}(OH)_{31}(SO_4)_2xH_2O$, according to the official monograph USP XX, third supplement USP-NF, and has a molecular weight of about 1097.4. Magaldrate, also sometimes referred in said monograph as aluminum magnesium hydroxidesulfate, contains not less than 29.0 percent and not more than 40.0 percent of magnesium oxide (MgO) and the equivalent of not less than 18.0 percent and not more than 26.0 percent of aluminum oxide ($Al_2O_3$).

The preparation of magaldrate is described in U.S. Pat. No. 2,923,660. A commercially suitable procedure is described in said patent, for example, beginning in column 2, line 40, although to maintain a low sodium content for the final product, the use of potassium oxide (or hydroxide) is preferred over the discloed sodium oxide. Typically the magaldrate is precipitated to provide a 6% weight/volume mixture (fluid when fresh) and diluted to 3% or washing prior to concentration and formulation into a suspension providing a so called single strength neutralization capacity (ANC) of 13.5 to 15 meq per 5 milliliters of suspension which is equivalent to a magaldrate weight/weight concentration in the range of about 12 to 13 percent solids. At this concentration, unformulated, magaldrate is a paste-like gel. In one commercial embodiment sold under the RIO-PAN trademark, the magaldrate is formulated with acacia gum to reduce the gel viscosity and achieve satisfactory fluidization. While acacia is suitable as a fluidizer for the so called single strength magaldrate product and is reported to be suitable for lowering the viscosity of a concentrated commercially aqueous antacid gel cake consisting of aluminum or magnesium hydroxide or a physical mixture of the two hydroxides, the same is not suitable for providing a magaldrate product providing greater than about 22 milliequivalents per 5 ml of ANC and the high antacid capacity composition of this invention. It is hardly surprising that the usefulness reported for acacia in liquifying aluminum or magnesium hydroxide antacids or mixtures thereof does not extend to magaldrate, since their crystal structures have been reported to be distinct. Thus, while magaldrate has a great similarity structurally to the naturally occurring minerals hydrotalcite and motukoreaite, and is believed to contain sulfate as the major interlayer, with a small amount of carbonate impurity, magnesium hydroxide is most similar to the mineral brucite and aluminum hydroxide has a disordered, amorphous polymeric structure. The physical mixtures of some aluminum and magnesium hydroxides have been reported to form hydrotalcite type structures on aging while retaining many brucite characteristics.

Mere fluidization or defloculation of an aqueous suspension dosage is, however, only one factor in the formulation of an aqueous antacid susension. Thus, no advantage arises from increased fluidization of more highly concentrated suspension if fluidization is achieved at the expense of resuspendibility or loss of rate or extent of acid neutralization capacity or antacid buffer capacity, immediately or upon aging. This concern is especially acute for an aqueous antacid suspension comprising magaldrate as the predominant antacid because of its exceptional balance of desirable antacid properties within a single chemical entity—i.e., rapid reaction rate, prolonged buffering action within the therapeutically desired range and good acid-consuming capacity. With this invention, the desirable balance of magaldrate antacid properties is retained while the rheological properties of the magaldrate gels are significantly altered, thereby enabling the provision of concentrated, high antacid capacity magaldrate suspension. An additional benefit accompanying this invention is the uniformity of desirable rheological properties obtained which reduces or eliminates the batch to batch fine tuning frequently required to deal with the unpredictability usually inherent in the rheological properties of both fluidized and unfluidized magaldrate gels.

Accordingly this invention relates to an aqueous antacid composition characterized in providing a fluid, resuspendible, pharmaceutically elegant antacid suspension with high antacid capacity. This composition comprises precipitated and undried magaldrate gel and a fluidizing amount of a combination of an aluminum hydroxide gel having colloidal properties as a first fluidizer and a second fluidizer selected from at least one from the group consisting of citric acid and a pharmaceutically acceptable citrate ion source.

As previously described the magaldrate gel of this invention refers to precipitated magaldrate which has not previously been dried to its hydrated, anhydrous form. While the fluidizing combination contained in the composition of the invention may very well fluidize an aqueous mixture employing anhydrous magaldrate gel, a composition therefrom will not possess the desirable combination of suspension, resuspendibility, colloidal and antacid properties provided by the composition of the invention. Moreover, it is preferred in the composition of the invention to utilize freshly precipitated magaldrate gel since the use of older gels appears to require relatively higher proportions of the fluidizing combinations than the same composition comprising freshly precipitated magaldrate gels.

In contrast to most currently available antacid suspensions and to commercial magaldrate antacid suspensions which provide an ANC of about 13.5 meq/5 ml, the composition of this invention readily provides an acid neutralization capacity (double strength) of at least 25-30 meq/5 ml or of at least about 17-18% to about 20% weight/weight or about 18 to about 22% weight/volume. It will be appreciated that less concentrated suspensions such as those having an ANC of 13.5 meq/5 ml are, also, easily achievable by the composition and method of this invention. The upper limit to the ANC and concentration of the composition of this invention is only limited by the equipment available, but is believed to be on the order of 50-60 meq/5 ml.

The ratio on a dry basis of magaldrate to the fluidizing combination will range from about 25:1 to about 2:1, and preferably from about 8:1 to about 4:1. For example, in a composition having 216 g magaldrate per liter of suspension, the 25:1 to 2:1 ratio would correspond to about 8.0 g/l to about 104 g/liter of fluidizers.

The ratio on a dry basis of the first fluidizer, aluminum hydroxide gel, calculated as aluminum oxide to the second fluidizer will range from about 1:15 to about 1:1, preferably from about 1:6 to about 1:2 and most preferrably in a range of about 1:4. For example, in a composition having 216 g magaldrate per liter of suspension in a ratio to fluidizers of 8:1 or 27 g/l of fluidizers the 1:4 ratio of first fluidizer to second fluidizer would correspond to about 5.4 g/l of first fluidizer and 21.6 g/l of second fluidizer.

In another embodiment, the invention relates to a method for providing or preparing aqueous antacid comositions of high antacid capacity and which are further characterized in providing fluid, resuspendible pharmaceutically elegant antacid suspensions of magaldrate. The method broadly comprising mixing a precipitated and undried magaldrate gel with a fluidizing combination of the first and second fluidizer of this invention. Moreover, mixing can be done prior or subsequent to concentration of the magaldrate gel.

Thus in one aspect the method of this invention comprises:

(a) mixing a low concentration of a precipitated and undried magaldrate gel with a fluidizing amount of a combination of an aluminum hydroxide gel having colloidal properties as a first fluidizer and a second fluidizer selected from at least one from the group consisting of citric acid and a pharmaceutically acceptable citrate ion source;

(b) concentrating the mixture of step (a) to a fluid high antacid capacity aqueous magaldrate suspension.

Alternatively, the steps of the method of the invention may be reversed so that the magaldrate gel is first concentrated to a concentration providing a high antacid capacity and then fluidized by mixing the concentrate magaldrate gel with a fluidizing amount of a combination of the first and second fluidizer of the invention.

In a preferred embodiment the method of the invention comprises:

(a) forming an aqueous mixture containing a fluidizing amount of a combination of an aluminum hydroxide gel having colloidal properties as a first fluidizer and a second fluidizer selected from at least one from the group consisting of citric acid and a pharmaceutically acceptable citrate ion source;

(b) concentrating a precipitated and undried magaldrate gel to high antacid capacity;

(c) incrementally and continuosly charging and mixing the concentrated magaldrate gel into a stream of the mixture containing said fluidizers thereby fluidizing the concentrated gel into a fluid suspension; and (d) incrementally and continuously charging and mixing additional concentrated magaldrate gel into a continuosly recycled stream of the increasingly concentrated fluidized suspension to provide a fluidized high antacid capacity magaldrate suspension.

The concentrations and proportions of materials used in the method of the invention are the same as those described for the composition of the invention and will be based on the magaldrate concentration of the fluidized suspension. Thus, the concentration of the magaldrate in step (b) of the hereinabove described method will exceed the final concentration of the suspensions. Also, as with the composition of the invention, the method of the invention preferably employs freshly precipitated magaldrate gel.

The composition of the invention can also and usually does include a number of pharmaceutically acceptable excipients which are conventional in the aqueous antacid suspension art and do not form part of the invention. Such excipients include one or more flavoring agents e.g. peppermint, etc; sweetening agents, e.g. saccharin, sorbitol, preservatives; sanitizers; body-building agents and the like.

The composition of this invention may also contain other therapeutically active substances such as antiflatulents, as for example, simethicone, algin derivatives for treatment of esophogeal reflux; analgesics such as acetaminophen, ibuprofen and protected aspirin; various antidiarrheal or parasympatholytic agents; antiulcer agents such as cimetidine, ranitidine and sucralfate; and others.

Compositions of this invention are useful in the treatment of a variety of gastrointestinal disorders in man or animals. Typical of such disorders are hyperchlorhydria, peptic ulcer, gastic ulcer, duodenal ulcer, gastritis, esophagitis, hiatal hernia, and other digestive disturbances. As noted earlier, the composition of this invention is especially useful in the treatment of disorders that demand the antacid to play a therapeutic role rather than a mere pallative role. The dosage form for the composition of this invention will normally be administered orally. In general, the therapeutic dosage of the composition can be determined by relationship to the ANC of same to that of known antacid dosage forms.

While not wishing to be bound by any theory of invention, it is hypothesized that magaldrate prepared by the processes earlier described, contains small particles with a resulting greater surface area and higher surface charges. With a material such as just described, one in which it is essential to maintain the colloidal properties of the magaldrate to guarantee its most efficacious values over a useful shelf-life, control of viscosity is critical, and, is rendered more difficult in increasing concentrations. This control is achieved with a fluidizing amount of a combination of the first and second fluidizer whereby the second fluidizer apparently controls the surface charge of the magaldrate to create a desirable negative influence while the first fluidizer apparently enhances the anion adsorption process a provides a competitive substrate with the magaldrate thereby maintaining an equilibrium of the negative influence. The negative influence, which can be determined by zeta potential measurements, thus fluidizes the magaldrate suspension to a mobilizable gel having an equilibrium which apparently provides for retention of desirable properties.

The invention may be further illustrated by the following examples. In example 1-3 the magaldrate gel (potassium base) was first concentrated to about a 24% w/w strength at which point it was a stiff immobile paste and then used to prepare the composition listed.

EXAMPLE 1

| Ingredients | Amount (mg) |
| --- | --- |
| Magaldrate Gel | 152.5 |
| Aluminum Hydroxide (colloidal) | 7.4 |
| Potassium Citrate | 30.8 |
| Saccharin | 0.4 |
| Sorbitol Solution (70%) | 100.0 |
| Peppermint Flavor | 0.2 |
| Orange Flavor | 2.0 |
| Water q.s. | 1000.0 |

This composition provided a magaldrate suspension according to the invention having 15.2% magaldrate solids providing approximately 20 meq/5 ml of ANC.

The citrate was dissolved in sufficient water to make an 80% w/w solution. The citrate solution and the aluminum hydroxide which is provided as a paste (12.5–13.5% Al$_2$O$_3$) were added to the concentrated magaldrate gel paste. The mixture was blended until it became a mobile liquid suspension. The other ingredients were then added to the suspension, the water being last to provide the final weight. The mixture was further blended to yield a homogeneous suspension. The final suspension was then further homogenized prior to filling the palatable suspension into 12 fluid ounce container for stability observation.

The suspension was evaluated over a four month period. At each time point, the suspension was found to have maintained its initial ANC, physical appearance, particle size distribution, mobility and resuspendibility (5 hand shakes).

EXAMPLE 2

| Ingredient | Amount (mg) |
| --- | --- |
| Magaldrate Gel | 170.8 |
| Aluminum Hydroxide (colloidal) | 8.1 |
| Potassium Citrate | 34.2 |
| Saccharin | 0.4 |
| Sorbitol Solution (70%) | 50.0 |
| Gylcerine | 50.0 |
| Peppermint flavor | 0.3 |
| Water q.s. | 1000.0 |

The magaldrate composition of the invention in this example provided a suspension having about 17.1% magaldrate solids with an approximate ANC of 24 meq/5 ml.

The composition of this example was prepared as described in Example 1 and with the same results.

EXAMPLE 3

| Ingredients | Amount (mg) |
| --- | --- |
| Magaldrate Gel | 201.3 |
| Aluminum Hydroxide (colloidal) | 10.5 |
| Potassium Citrate | 40.1 |
| Saccharin | 0.4 |
| Sorbitol Solution (70%) | 80.0 |
| Glycerine | 20.0 |
| Lemon Flavor | 2.7 |
| Peppermint Flavor | 0.2 |
| Water q.s. | 1000.0 |

The approximate ANC of this 20.1% w/w magaldrate is about 29 meq/5 ml.

The composition of this example again provided a fluid suspension and was prepared as described in Example 1 with the same results.

EXAMPLE 4

A magaldrate suspension product, according to the invention, having an ANC of 30 meq/5 ml or magaldrate 1080 mg/5 ml of suspension was prepared as follows. The formula given is for 1 liter (1.18 Kg).

| Ingredient | Amount |
| --- | --- |
| Magaldrate Gel | 2.93 l* |
| Aluminum Hydroxide Gel (12.5% Al$_2$O$_3$) | 47.8 g |
| Potassium Citrate | 19.6 g |
| Sorbitol Solution (70%) | 57.4 g |
| Glycerin | 47.8 g |
| Saccharin | 0.383 g |
| Xanthan Gum | 1.43 g |
| Peppermint, Natural and Artificial | 0.283 ml |
| Monochloramine Solution | q.s. |
| Water, purified, Chlorinated q.s. | 1.18 Kg. |

*Theoretical input per liter is 216 g Magaldrate at 100%

1. In a suitable tank equipped with a mixer, the sorbitol solution, 15.7 g of the water and the citrate were combined and then mixed until a clean solution was obtained. The aluminum hydroxide gel was added and mixed until uniform and mixing continued until use.

2. Immediately before concentration of the magaldrate gel, 126 g of the Step #1 mixture was added to a jacketed tank equipped with a stirrer. With continuous stirring, the magaldrate gel was concentrated on a rotary filter to a concentration of not less than 24% w/w into the mixture and cooling to 25° C. was begun. After all the concentrated had been added the remainder of the Step #1 mixture was added with continuous stirring to achieve uniformity.

3. The Step #2 mixture was poured through a homogenizer into a jacketed tank with continuous stirring and continuous cooling to 25° C.

4. The remaining ingredients, except the water and monochloramine, were mixed in a separate container until uniform, after which, they are added to the magaldrate mixture and mixed until the xanthan gum was hydrated. Water was then added (with mixing) to bring the batch up to about 1.18 Kg.

5. Prior to filling the suspension, sufficient monochloramine was added to and mixed into the bulk material to provide at least 85 ppm in the suspension.

6. The suspension was then filled into sterilized containers which were capped, inverted and returned to the upright position.

The suspension of this example was subjected to repeated freeze-thaw cycles of 24 hours each, and after each cycle both the physical and antacid properties were retained. In contrast, a conventional magaldrate suspension at even 13.5 meq/5 ml with acacia as the deflocculant did not retain all the properties after only one such cycle.

EXAMPLE 5

Using the procedure described in Example 4, a magaldrate suspension, according to the invention, having an ANC of about 45 meq/5 ml may be prepared.

| Ingredients | Amount |
| --- | --- |
| Magaldrate Gel (at about 34%) | 985.0 g |
| Aluminum Hydroxide Gel (Al$_2$O$_3$ 12.5%) | 47.8 g |
| Polassium Citrate | 39.2 g |
| Sorbitol Solution (70%) | 57.4 g |
| Glycerin | 47.8 g |
| Saccharin | 0.383 g |
| Xanthan Gum | 1.43 g |
| Peppermint Flavor | 0.283 ml |
| Monochloramine Solution q.s. | 100 ppm |
| Water, purified, chlorinated q.s. ad | 1.0 L |

EXAMPLE 6

A magaldrate suspension, according to the invention, was prepared with the formula and procedure described in EXAMPLE 4, but for the addition of simethicone to provide a suspension with an ANC of 30 meq/5 ml and 30 mg/5 ml of simethicone.

EXAMPLE 7

| Ingredient | Amount A | B |
| --- | --- | --- |
| Magaldrate Gel at 27.6% w/w or 24.14% w/w/ | 1565 g | 1789 g |
| Aluminum Hydroxide Gel (13.5% Al$_2$O$_3$) | 86.04 | 100.4 g |
| Potassium Citrate Solution (80%) | 61.9 | 137.6 g |
| Sorbitol Solution (70%) | 114.8 g | |
| Glycerin | 95.6 g | |
| Saccharin | .766 g | |
| Xanthan Gum | 2.86 | 3.43 g |
| Peppermint Flavor | 0.57 ml | |
| Monochloramine Solution q.s. | 100 ppm | |
| Water, distilled q.s. | 2.321 Kg | |

In this experiment, two different freshly concentrated magaldrate gels at the percents indicated were employed to prepare suspensions with an ANC of 30 meq/5 ml. The sorbitol, citrate, and aluminum hydroxide gel were added to a container equipped with a stirrer and mixing was begun. The magaldrate was added to the same container, preferrably incrementally and mixed until uniform. The saccharin and flavor were dispensed in the glycerin, after which, the xanthan gum was added and mixed until uniform. The flavored dispension was then added to the fluidized magaldrate with mixing until the mixture was uniform and the gum hydrated. Sufficient distilled water was added with mixing as was a quantity of the chlorine sanitizing solution to provide about 100 ppm chlorine. The suspensions (12) having an aluminum oxide ratio to citrate ranging from about 1:8.8 to about 1:3.95 were then filled into container. All formulations provided suspensions with the desired physical and antacid properties including resuspendibility.

EXAMPLE 8

A typical formulation for the monochloramine solution referred to in some of the prior examples as follows:
Calcium Hypochlorite 60%: 14.0 g
Ammonia Solution, Strong: 7.4 g
Water, purified, chlorinated: 1998. g

What is claimed is:

1. An aqueous antacid composition characterized in providing a fluid resuspendable pharmaceutically elegant antacid suspension with high antacid capacity of at least about 25 milliequivalents of acid neutralizing capacity per 5 milliliters of suspension consisting essentially, prior to forming the pharmaceutically elegant antacid suspension, of:

(a) precipitated and undried magaldrate gel containing at least about 24% by weight of magaldrate, and (b) a fluidizing amount of a combination of (i) an aluminum hydroxide gel having colloidal properties of a first fluidizer and (ii) as a second fluidizer potassium citrate, the weight ratio on a dry basis of magaldrate to the combination of fluidizers being within the range of about 25:1 to 2:1 and the weight ratio on a dry basis of the first fluidizer calculated as aluminum oxide and the second fluidizer being within the range of about 1:6 to about 1:2.

2. The composition of claim 1 wherein the ratio on a dry basis of magaldrate to the combination of fluidizers ranges from about 8:1 to about 4:1.

3. The composition of claim 1 wherein the ratio on a dry basis of the first fluidizer to the second fluidizer is about 1:4.

* * * * *